United States Patent
Hasegawa et al.

(10) Patent No.: US 6,296,860 B1
(45) Date of Patent: Oct. 2, 2001

(54) COATED PIGMENTS AND EXTENDER PIGMENTS, AND COSMETICS CONTAINING THE SAME

(75) Inventors: Yukio Hasegawa, Koshigaya; Taizo Miyoshi, Yono; Ryo Ohara, Urawa, all of (JP)

(73) Assignee: Miyoshi Kasei, Inc., Saitama (JP)

( * ) Notice: Subject to any disclaimer, the term of this patent is extended or adjusted under 35 U.S.C. 154(b) by 0 days.

(21) Appl. No.: 09/267,348

(22) Filed: Mar. 15, 1999

(51) Int. Cl.[7] .................................................. A61K 6/00
(52) U.S. Cl. .................................. 424/401; 424/63; 424/69
(58) Field of Search ................................ 424/63, 489, 401, 424/64, 69, 365

(56) References Cited

U.S. PATENT DOCUMENTS 4,606,914 * 8/1986 Miyoshi .................................. 424/63

FOREIGN PATENT DOCUMENTS 0 139 481  5/1992  (EP) .
2676922  12/1992  (FR) .
2698869   6/1994  (FR) .

* cited by examiner

Primary Examiner—Thurman K. Page
Assistant Examiner—Blessing Fubara
(74) Attorney, Agent, or Firm—Armstrong, Westerman, Hattori, McLeland & Naughton, LLP (57) ABSTRACT

Pigments and extender pigments coated with a mixture comprising at least N-acyl forms of naturally existing 14 amino acids, in particular, pigments and extender pigments processed with a mixture comprising at least N-acyl forms of 14 amino acids, obtainable from or obtained on hydrolysis of any one of animal proteins, such as silk and pearl, and plant proteins, such as wheat and soybeans, which can be mixed into cosmetics, and also cosmetics comprising the coated pigments and extender pigments are provided. Such N-acyl form therein may be in the salt form. The obtained pigments and extender pigments coated therewith in the present invention has extremely smooth tactile feeling, that is an optimum affinity to skin and/or hair (biocompatibility) when used in cosmetics, excellent application feeling on skin and/or hair without coarse feeling, and hence suitable for the powders in cosmetics to be combined.

9 Claims, 1 Drawing Sheet

COATED PIGMENTS AND EXTENDER PIGMENTS, AND COSMETICS CONTAINING THE SAME

BACKGROUND OF THE INVENTION

1. Field of the Invention

The present invention relates to novel coated pigments and extender pigments, particularly novel coated material in a finely pulverized (powdered) state, that is novel coated pigments and extender pigments, usable for cosmetics, and novel cosmetics containing the coated pigments and extender pigments.

More particularly, it relates to the pigments and extender pigments, coated with a mixture comprising at least 14 acylated amino acids or salts, with the amino acids being obtainable from or obtained on total hydrolysis of any one of animal proteins, such as silk and pearl, and plant proteins, such as wheat and soybeans, and cosmetics containing such pigments and extender pigments. The pigments and extender pigments, coated with a mixture comprising at least 14 acylated amino acids, wherein said amino acid may be in the salt form in one or more of 14 amino acids, presents extremely smooth feeling and exhibits superior cohesion to skin and hair (biocompatibility), so that cosmetics comprising the pigments and extender pigments is retained to be highly promising as cosmetics exhibiting these desirable properties.

2. Description of the Related Art

The pigments and extender pigments, added to cosmetics, especially inorganic pigments, are poor in its ability to spread (spreadability), hard and heavy (coarse), that is devoid of elasticity, and present a dragging feeling, thus giving physical irritation to the skin. Moreover, since it is inorganic, it exhibits poor affinity to skin. Meanwhile, good affinity to the skin means having light touch on the skin and favorable feeling to the skin. For overcoming these defects, a number of types of coated pigments and extender pigments, that is surface-processed pigments and extender pigments, has been proposed. For example, there are so far known a number of different methods, such as a method of surface-coating with ester oils, metal soap, lecithin, silicone oil or perfluoro alkyl oil, or a method of coating with a sole acylated amino acid or an acylated form of a polypeptide, which is a polymer of the amino acid see Japanese Patent Kokai Publication JP-A-61-73775.

PROBLEMS TO BE SOLVED BY THE INVENTION

In the course of the completion to the present invention, the following problems have also been found by the present inventors and the present invention.

In view of the above related art references, the above-mentioned known techniques suffer from a number of drawbacks.

The pigments and extender pigments, coated with ester oils, metal soap, lecithin, silicone oil, or perfluoro alkyl oil, while presenting a smooth tactile feeling and a reduced physical stimuli to the skin, is poor in compatibility to the human body, such that it is poor in affinity to the skin.

It has been known to coat the pigments and extender pigments with amino acids or polypeptides to improve affinity to the skin, as disclosed in Japanese Patent Kokoku Publication JP-B-1-50202, and Japanese Patent Kokai Publications JP-A-61-73775, JP-A-61-10503, JP-A-61-7207, JP-A-61-69709, JP-A-5-186706, JP-A-3-200879, JP-A-9-328413, and JP-A-10-226626. Although these publications state that the coated pigments and extender pigments exhibits smooth tactile feeling and high affinity to the skin, the meritorious effect of the coated pigments and extender pigments can not be said to be optimum.

The pigments and extender pigments, coated with N-acylated amino acid, as described in Japanese Patent Kokoku, Publication JP-B-1-50202, such as with N-acyl-L-glutamic acid, N-methyl-N-methyl glycine or with N-acyl-N-methyl-β-alanine, while having a smooth tactile feeling, is not optimum in affinity to the skin.

The pigments and extender pigments, coated with N-acylated peptide, is poor in smoothness and also has objectionable physical stimuli, due to the hard and heavy (coarse) feeling associated with polypeptides (refer to Japanese Patent Kokai Publication JP-A-61-73775).

The pigments and extender pigments, coated with N-mono long-chain basic amino acid, while presenting smooth tactile feeling, is not optimum in affinity to the skin due to the presence of basic amino acids (see Japanese Patent Kokai Publications JP-A-61-10503, JP-A-61-7207, JP-A-61-69709 and JP-A-5-186706).

Similarly to the subject-matter of the Japanese Patent Kokoku Publication JP-B-1-50202, the pigments and extender pigments coated with N-acylated aspartic acid, while presenting smooth tactile feeling, is not optimum in affinity to the skin (see Japanese Patent Kokai Publication JP-A-3-200879).

Therefore, similarly to the pigments and extender pigments, coated with the N-acylated peptide, the above pigments and extender pigments is also not desirable in smoothness of touch or affinity to the skin (As for the pigments and extender pigments coated with the N-acylated silk peptide, disclosed in Japanese Patent Kokai Publication JP-A-9-328413, see Japanese Patent Kokai Publication JP-A-61-73775.).

The pigments and extender pigments, coated with sericin, which contains a large quantity of serine, as one of hydroxy-amino acids retained to be usable in place of AHA (α-hydroxy acid), is improved in affinity to the skin (see Japanese Patent Kokai Publication JP-A-10-226626). However, smooth tactile feeling can not be obtained with this material. For the above reason, it has long been a desideratum to develop coated pigments and extender pigments having agreeable feeling on application and superior affinity to the skin or hair.

It is an object of the present invention to provide pigments and extender pigments having a smooth tactile feeling when used in cosmetics and excellent cohesion to the skin or hair, that is, having superior affinity to the skin or hair (biocompatibility). It is another object of the present invention to provide cosmetics having the above desirable properties by having the above pigments and extender pigments contained therein.

SUMMARY OF THE INVENTION

The present inventors have conducted perseverant researches towards resolving the above problems and found that the coated pigments and extender pigments comprising pigments and extender pigments, which is a material in a finely pulverized state, coated with a mixture comprising at least N-acyl forms of 14 amino acids specified by glycine, L-alanine, L-valine, L-leucine, L-isoleucine, L-phenylalanine, L-proline, L-threonine, L-serine, L-arginine, L-histidine, L-lysine, L-aspartic acid and L-glutamic acid, more preferably, coated with a mixture comprising at least N-acyl forms, of the 14 amino acids, obtainable or obtained on acylating amino acids comprising at least the 14 amino acids, represented by the following general formula:

(1)

and being obtainable on total hydrolysis of at least one protein type particularly preferably derived from animal proteins, such as silk and pearl, and plant proteins, such as wheat and soybeans, wherein $R_1$ is an alkyl group of C8 to C22 carbons which may contain carbon-carbon double bond and/or triple bond in the molecule, such as alkenyl, saturated or unsaturated, or a hydrocarbon group of the alicyclic structure of C8 to C22 carbons, saturated or unsaturated, is any amino acid residue of the 14 amino acids, specifically, any of glycine, alanine, valine, leucine, isoleucine, phenylalanine, proline, threonine, serine, arginine, histidine, lysine, aspartic acid and glutamic acid residues, M is one of H, Na, K, polyvalent metal, such as Ba, Zn, Ca, Mg, Fe, Zr, Co, Al and Ti, ammonium, and an onium of organic alkanol amines, such as monoethanol amine, diethanol amine, triethanol amine, 2-amino-2-methyl-propanol, 2-amino-2-methyl-1, 3-propanediol and triisopropanol amine, has extremely smooth tactile feeling and superior affinity to skin and hair and moreover is particularly suited to addition to cosmetics. In the above cases, such N-acyl form may be in the salt form, and therefore such N-acyl form includes one in the free form and/or the salt form.

This finding led to the completion of the present invention.

Specifically, the present invention contains the followings:

1. The coated pigments and extender pigments usable in cosmetics comprising pigments and extender pigments, said pigments and extender pigments being coated with a mixture comprising at least N-acyl forms of 14 amino acids specified by glycine, L-alanine, L-valine, L-leucine, L-isoleucine, L-phenylalanine, L-proline, L-threonine, L-serine, L-arginine, L-histidine, L-lysine, L-aspartic acid and L-glutamic acid, wherein the N-acyl amino acid may be in the salt form, that is, may include one in the free form and/or one in the salt form;

The 14 amino acids in the present invention are isomeric L-forms existing in nature or available from the natural world. However, glycine does not have an asymmetric carbon atom, and thus does not have such isomeric form, L- or D-form. In a majority of cases, amino acids have isomers. In such amino acids, the amino acids may be used as a mixture or a compound of isomers insofar as the amino acids contain isomers existing in nature or available from the natural world, that is, L-form. If, for example, there exist D- and L-forms, the L-forms exist in nature. In such amino acids, amino acids of the DL-forms can be used in the present invention insofar as the amino acids contain amino acid L-form existing in nature. It is also possible for the mixture containing the N-acyl form used in the present invention to contain further N-acyl forms of any L-amino acids other than those used in the present invention, such as L-tyrosine, L-methionine, L-cystine and L-cystein, and N-acyl forms of any isomers of amino acids other than those mentioned above (glycine and the 13 L-amino acids), and other materials other than amino acids and derivatives thereof, provided that the mixture contains the above-mentioned 14 N-acyl forms used in the present invention.

In basic amino acids, having plural amino groups, including imino groups, such as lysine, it suffices if the N-acyl form is a derivative at least one N-position of which is acylated.

The N-acyl form of amino acids, used in the present invention, may be in a free form or in a salt form. In the latter case, the forms or the bases for the salts of the amino acid derivative in the salt forms are independent of one another, and may be all or partly the same or different forms or bases for such salts.

It suffices if the amino acid as a starting material is in the natural form (L-form except for glycine) and may be in the form of a mixture if only it contains the isomer. There is no limitation to the manufacturing routes. Therefore, amino acids produced by a variety of manufacturing methods, such as extraction, synthesis and microbiological manufacturing method, and a protein or peptide hydrolysis method, may be used. It is noted that such amino acids other than glycine are of the L-forms.

The coating method for pigments and extender pigments (a finely pulverized material) may be any of known coating methods used conventionally for modification of the pigments and extender pigments which have been used in the field of the cosmetics since the past time.

2. The coated pigments and extender pigments as defined above wherein at least a part (all or a part thereof) of the 14 amino acids is at least one of amino acids which can be obtained from a total hydrolysate (hydrolyzate) of protein;

3. The coated pigments and extender pigments as defined above wherein the protein is obtainable from or is, at least one of animal proteins, such as silk, pearl, collagen, keratin and the like, and plant proteins, such as wheat, soybeans and the like, containing the 14 amino acids as main amino acid constituents therein;

4. The coated pigments and extender pigments as defined above wherein the mixture comprising at east N-acyl forms of the 14 amino acids comprises 14 acylated amino acids, which can be obtained on acylating amino acids containing at least the 14 amino acids, represented by the following general formula wherein the N-acyl form may be in the salt form:

(1)

and being obtainable or obtained on total hydrolysis of at least one protein type, wherein $R_1$ is an alkyl group or a hydrocarbon group of the alicyclic structure, each having C8 to C22 carbons, saturated or unsaturated, is an amino acid residue, specifically, any of glycine, alanine, valine, leucine, isoleucine, phenylalanine, proline, threonine, serine, arginine, histidine, lysine, aspartic acid and glutamic acid residues, M is one of H (hydrogen atom), metal atom, ammonium and an onium of organic alkanol amine;

5. The coated pigments and extender pigments as defined above wherein the metal atom is any one of Na, K, Ba, Zn, Ca, Mg, Fe, Zr, Co, Al and Ti and the organic alkanol amine is any one of monoethanol amine, diethanol amine, triethanol amine, 2-amino-2-methylpropanol, 2-amino-2-methyl-1, 3-propane diol and triisopropanol amine;

6. The coated pigments and extender pigments as defined above wherein at least a part of the 14 amino acids is one or more amino acid(s) obtainable or obtained, on total hydrolysis of a protein derived from at least one of silk and pearl;

7. The coated pigments and extender pigments as defined above wherein the pigments and extender pigments is coated with a mixture containing N-acyl form of amino acids obtained on total hydrolysis of at least one of proteins selected from silk, pearl, collagen, keratin, wheat, soybean and the like;

According to the present invention, any pigments and extender pigments, coated with a mixture containing at least N-acyl forms of the above-mentioned 14 amino acids can be used for the coated pigments and extender pigments of the present invention. It is desirable for imparting smoothness to contain further one or more naturally existing amino acids (L-forms), in addition to the above 14 amino acids, as the amino acids in the N-acylated amino acids used for the present invention. Moreover, from the phase of manufacture, it is preferred to coat the pigments and extender pigments with a mixture obtained on total hydrolysis of a protein such as silk followed by N-acylation. The examples for the amino acids desirable to be additionally contained may be specified by L-tyrosine, L-methionine, L-cystine, L-cystein and the like.
and 8. The cosmetics comprising coated pigments and extender pigments as defined in any one of the above items 1 to 7.

In the mixing method for such pigments and extender pigments in the present invention to make the cosmetics, any suitable methods so far known for mixing or combining the known powdered materials or another known coated powdered materials as used for the cosmetics, into the cosmetics in making the cosmetics can be employed.

PREFERRED EMBODIMENTS OF THE INVENTION

The coated pigments and extender pigments for mixing to cosmetics according to the present invention is at least part in pigments and extender pigments mixed into cosmetics and which (said at least part thereof) is surface-coated by processing with a mixture comprising N-acylated 14 amino acid derivatives which may include one or more free forms and/or salt forms. Although the above 14 amino acids are sufficient as amino acids for N-acylation, it is desirable that naturally existing amino acids (L-forms) be further contained in the mixture for further improving the smoothness.

As amino acids prior to acylation according to the present invention, naturally existing amino acids are desirable. As the starting materials, the amino acids obtainable or obtained, on total hydrolysis of one or more proteins mainly containing the above 14 or more, and in particular the above 14 amino acids, such as animal proteins, including silk, pearl, collagen and keratin, and plant proteins, such as wheat and soybeans, are desirably used. Most simply, the amino acid mixture resulting from the total hydrolysis are N-acylated and applied to the pigments and extender pigments for coating.

As silk, cocoons of silk worms, raw silk, cocoon wastes, raw silk yarn waste, silk yarn, silk cloth wastes and the like, may be used. As pearl, various fish shells, such as mussels, fresh-water mussel, hard-shelled mussel, Mytilidae, Bivalvia and the like, may be used. As collagen, skin tissue of cows or ox, soft bone and pork skin, collagen protein extracted from the connective tissue of hard fish, such codfish, a flatfish, flounder, sardine, salmon, trout, mackerel, tuna and grouper, Daucus Carota (plant) and the like may be used. As keratin, wool, animal hair, human hair, feather, nail, cone and keratin of plant origin, such as soybean, wheat, barley, corn, sesame and millet, may be used.

As for the tactile feeling, pigments and extender pigments coated with pearl amino acid or its salts or acylated silk composed mainly of acylated forms of total hydrolysates (hydrolyzates) of silk fibroin and conchyolin, containing an abundant quantity of alkyl amino acids such as glycine and alanine, are desirable.

For economic reasons, the pigments and extender pigments coated with acylated silk amino acids, which may be in the salt form, mainly composed of acylated total hydrolyzates (hydrolysates) of silk fibroin are preferred.

The acylated amino acids used in the present invention may be prepared using known methods, such as those disclosed in Japanese Patent Kokai Publication JP-A-6-256274 or Japanese Patent Kohyou Publication JP-A-7-502010.

For example, hydrolysis of silk yarn of cocoons with strong acids, such as hydrochloric acid or sulfuric acid, gives peptides, such as fibroin or sericin. On further hydrolysis, these peptides are turned into amino acids which then may be acylated with long-chain fatty acids with 9 to 23 carbon atoms and occasionally turned into salts, where necessary. The amino acids used in the present invention are in the form of a mixture of non-polymerized sole amino acids. In the above general formula (1), $R_1$ denotes alkyl or alicyclic hydrocarbon residues with 8 to 22 carbon atoms of long-chain fatty acid residues, which may occasionally contain any unsaturated carbon-carbon bonds. The constituent fatty acids for N-acylation in the present invention may include capric acid, lauric acid, myristic acid, isomyristic acid, palmitic acid, isopalmitic acid, stearic acid, isostearic acid, arachic acid, undecylenic acid, oleic acid, myristic acid, elaidic acid, linolic acid linoleic acid, arachidonic acid, palm oil fatty acid, beef tallow fatty acid and resin acid (abietic acid).

The acylamino acids used in the present invention are preferably in the polyvalent salts since then the acids are hydrophobic.

The acylamino acids may be marketed or purchased ones, such as "C8 SOIE HYDRO", "C12 SOIE Na " and "C16 SOIE ACIDE ", which are marketed by PHYTOCOS, France, and "amino-form W" (Croda, Japan), "Crosilk A/S" (Croda, UK).

Examples of amino acid compositions derived from animals such as silk and pearl, and plants such as wheat and soybean, constituting the side chain $R_2$ in the above general formula (1), are shown in Table 1 Since the 14 amino acids are contained therein, the mixture of the N-acyl forms obtained from the amino acid compositions as shown in the table are included in the mixture containing at least N-acyl forms of the 14 amino acids used in the present invention.

TABLE 1

Amino Acid Composition of Starting Proteins (wt %)

| Amino acids | Silk | Pearl | Wheat | Soybean |
|---|---|---|---|---|
| Aspartic acid | 8.0 | 9.2 | 7.5 | 16.2 |
| Glutamic acid | 2.1 | 3.0 | 29.9 | 27.1 |
| Alanine | 25.4 | 14.0 | 6.6 | 6.0 |
| Arginine | 1.5 | 1.4 | 4.1 | 5.9 |
| Cystine | 0.2 | Trace | 1.1 | 0.5 |
| Glycine | 33.2 | 42.9 | 6.7 | 6.4 |
| Histidine | 0.4 | 0.2 | 2.0 | 2.1 |
| Isoleucine | 0.9 | 3.2 | 3.5 | 2.0 |
| Leucine | 3.1 | 6.3 | 8.0 | 6.4 |
| Lysine | 1.0 | 1.2 | 5.2 | 5.7 |
| Methionine | 0.1 | 0.4 | 1.1 | 1.3 |
| Phenylalanine | 0.5 | 1.2 | 2.0 | 2.9 |
| Proline | 0.6 | 2.7 | 6.9 | 5.7 |
| Serine | 18.1 | 7.5 | 5.9 | 6.0 |
| Threonine | 2.4 | 2.3 | 3.8 | 3.1 |
| Tryptophan | trace | Trace | trace | trace |
| Tyrosine | 0.6 | Trace | 0.3 | 0.3 |
| Valine | 1.9 | 4.5 | 5.4 | 2.4 |

There is no particular limitation to the pigments and extender pigments used in the present invention insofar as it is used routinely for cosmetics. The pigments and extender pigments for cosmetics which will be developed in the future may also be used.

For the pigments and extender pigments, the extender may be enumerated by, for example, mica, sericite, talc, kaolin, synthetic mica, calcium carbonate, magnesium carbonate, magnesium silicate, aluminum silicate, calcium phosphate, silicic anhydride, alumina, magnesium oxide, aluminum hydroxide, barium sulfate, magnesium aluminate silicate, magnesium aluminate metasilicate, and boron nitride. Also, the white pigments may be enumerated by titanium dioxide, zinc oxide and cerium oxide, the inorganic colored pigments may be enumerated by red iron oxide, yellow iron oxide, black iron oxide, chromium oxide, chromium hydroxide, berlin blue, ultramarine and the like for the pigments and extender pigments used. The pearl pigments may be also enumerated by bismuth oxychloride, mica titanium (titanium-coated mica) and fish scale foil. The organic resin powders may be also enumerated by nylon powders, polyethylene powders, polyurethane powders, polystyrene powders, methyl methacrylate, silicone powders, teflon powders, cellulose powders, polyvinyl pyrrolidone powders and the like. As other powders for the pigments and extender pigments, there are tar dye, as organic pigments, aluminum powders, stainless steel powders and the like.

The form of the pigments and extender pigments used may be plural mixtures, complex composite products, affixtures or the like known in the forms and proceses normally used for cosmetics. For example, these pigments and extender pigments may be compounded or doped, as the need arises. For example, the pigments and extender pigments comprised of inorganic colored pigments, such as red iron oxide, coated with silicic anhydride, powders comprised of nylon coated with white pigments, powders comprised of an extender coated with ultrafine particulate white pigment and the like are cited.

The type or the content of the pigments and extender pigments used for cosmetics is selected depending on the type objective, the configuration of the cosmetics and the like. For example, one or more of the above enumerated pigments and extender pigments may be used. The pigments and extender pigments developed in future may also be used. The type, amount or the using method is selected in association with the methods known for using the pigments and extender pigments usable for cosmetics or the methods which will be developed in the future.

The amount of the acylated amino acids coated on the pigments and extender pigments is about 0.1 to 30 wt % and preferably about 1.0 to 10 wt % based on the pigments and extender pigments, depending on the particle size, specific surface area or the surface properties of the pigments and extender pigments. If the amount of the acylated amino acids is fewer than 0.1 wt %, optimum tactile feeling can not be achieved, whereas, if it exceeds 30 wt %, not only economic losses are brought about, but also the smooth tactile feeling or affinity to skin or hair can not be improved.

These pigments and extender pigments can be coated in any known methods with acylated amino acids. For example, the water-soluble salts of the acylated amino acids are dissolved in water and the pigments and extender pigments is added thereto and dispersed finely. As the liquid dispersion is stirred, an aqueous solution of polyvalent metal ions containing salts of, for example, Mg, Ca, Co, Zn, Ba, Zr, Al, Ti or the like is applied thereto dropwise to effect the coating. The coated product is filtered, washed and subsequently dried. The water-insoluble acylated amino acid salts are dissolved in suitable solvents, such as ethyl acetate, mixed with the pigments and extender pigments and dried to give the coated pigments and extender pigments. The present invention, however, is not limited to this coating method.

The amount of the coated pigments and extender pigments incorporated into cosmetics, optionally selected depending on the properties of the cosmetics, is about 0.01 to 100 wt % based on the total composition. One or more different types of the pigments and extender pigments may occasionally be used, as the need arises.

It is sufficient in the present invention if the coated pigments and extender pigments, which is a coated powdered material, as obtained in accordance with the present invention is used in at least part of the pigments and extender pigments used in the cosmetics. However, the larger amount of the coated pigments and extender pigments is desirable in the present invention. For optimum effect, at least 10% and preferably not less than 50% of the pigments and extender pigments used in the cosmetics are thus coated pigments and extender pigments in accordance with the present invention.

The cosmetics to which are added the pigments and extender pigments coated with the acylated amino acid mixture may be enumerated by finishing cosmetics, such as powder foundation, liquid foundation, oily foundation, stick foundation, pressed powder, face powders, lipstick, lipgloss, rouge for bucca, eye-shadow, eye-brow, eye-liner, mascara, watery nail enamel, oily nail enamel, emulsion type nail enamel, enamel top coat and enamel base coat, cosmetics for skin, such as emollient cream, cold cream, white cream, lotion, aqueous cosmetics, beauty liquids, carmine lotion, liquid cleansings cream, cleansing cream, cleansing powders, cleansing foam, make cleansing and body gloss, cosmetics for hairs, such as hair gloss, hair cream, hair shampoo, hair rinse, hair coloring and hair brushing agents, others, such as cream and lotion against anti-sun burning or for sun-burning, soap, bath agents and perfumes.

The cosmetics comprising the pigments and extender pigments coated with the mixture comprising at least 14 acylated amino acid mixture, wherein the amino acid may be in the salt form, may be mixed with pigment dispersing agents, oil ingredients, surfactants, UV absorbing agents, antiseptics, anti-oxidants, film forming agents, humectants, thickeners, dyes, pigments or perfumes, used in routine cosmetics, as described above, and in the range without impairing the effects obtained in the present invention.

Explanation for Operation

The reasons why the pigments and extender pigments coated with the acylated amino acid mixture in the present invention presents extremely smooth tactile feeling and superior affinity to the skin or hair (biocompatibility) may be summarized as follows:

First, amino acids are basic components making up the protein of living organisms. Protein is a compound having diversified steric structure made up of thousands to tens of thousands of polymers larger in size than the polypeptides which are polymers of hundreds of amino acids. These proteins and polypeptides are composed of approximately 20 different amino acids and exhibit extremely high safety and adaptability to the living organisms and hence are suited as components of the cosmetics. However, since proteins exhibit immunological activity towards living organisms and are harder because of its steric structure, amino acids and polypeptides instead, are preferentially used in cosmetics.

It is felt that the higher the polymerization degree of the amino acids, the higher is the film forming (film-making) properties. However, higher polymerization means lower affinity or absorptivity to the skin and hair. In other words, the sole amino acids, that is monomeric amino acids, exhibit maximum affinity to the skin and hair. Therefore, the amino acids are said to exhibit the skin curing effects and hair damage recuperating effects.

Second, the merit of acylating the amino acid with alkyl or hydrocarbon group of the alicyclic structure, groups occasionally containing carbon-carbon unsaturated bond(s), such as alkenyl, saturated or unsaturated, and having 8 to 22 carbon atoms, is realization of the smooth and slippery tactile feeling characteristic of the higher fatty acids. The amino acid has diversified functional groups, such as —COO$^-$, —NH$_3^+$ or —OH$^-$, and is adsorbed with water molecules so that it exhibits water retention properties. In general, an oleophilic amino acid is thought to exhibit higher affinity to the skin and hair than the hydrophilic amino acid. For this reason, the amino acid is acylated with higher fatty acids and thereby rendered oleophilic to increase the affinity to the skin and hair. That is, since the N-acylated amino acid is able to simultaneously furnish water and oil, both needed by the skin and hair, which accounts for its superior affinity to the human body.

It has been found that the higher the polymerization degree of the amino acid, the more apparent is the tacky feeling and hardness proper to peptides, thus leading to loss of the satisfactory tactile feeling otherwise brought about by acylation. That is, the optimum tactile feeling can be obtained by acylating the amino acid instead of polypeptide. If the number of carbon atoms of the acyl group is less than 8, astringency irritation to the skin exists along with decreased tactile feeling are produced, whereas, if the number of the carbon atoms is larger than 22, heavy (coarse) tactile feeling and loss of smoothness are produced, which therefore are not preferable.

Third, there are approximately 20 amino acids making up the human organism. These amino acids are classified into alkylamino acids, such as glycine and alanine, oxyamino acids, such as serine, basic amino acids, such as lysine and arginine, acidic amino acids, such as glutamic acid and aspartic acid, and aromatic amino acids, such as tyrosine. A mixture of the amino acids obtained on total hydrolysis of at least one of proteins derived from animals, such as silk and pearl, and from plants, such as wheat and soybeans, contains the 14 or more amino acids as discussed above, with these amino acids being the same as the amino acids making up the living organisms. These various amino acids play complex roles in setting the affinity of the amino acid to the living organism, such that satisfactory affinity can not be yielded by sole amino acids or a mixture of a few amino acids. It is felt that the acylated amino acid mixture made up of a variety of amino acids exhibits optimum performance in smooth tactile feeling and affinity to skin and hair (bioadaptability).

The 14 or more amino acids used in the present invention may be manufactured by any of the synthesis, fermentation or extraction methods. Similar effects may be obtained on coating the pigments and extender pigments with a mixture of acylated sole amino acids. These methods, which should be included in the present invention, are much expensive under the current manufacturing technique, while they may be expected for future production methods with further technical improvements, and hence are not economically desirable at the present stage.

The various amino acids, obtained on total hydrolysis of the animal protein, such as silk and pearl, and plant protein, such as wheat and soybeans, are usually of different amino acid compositions due to difference in the starting materials. Our experiments indicate that the larger the proportion of 3 aminoacids, that is glycine and alanine as alkylamino acids and serine as oxyamino acid in the total amino acid composition, the higher is the affinity to the skin and hair.

In cosmetics, the tactile feeling is a very significant factor in its evaluation. Smooth spreadability on application to the skin without abrasion and rough feeling is crucial. The abrasion or rough feeling is termed physical irritation and causes skin roughness and inflammation to the skin. The affinity is classed under an item of finishing of the cosmetics achieved by lightness of load on the skin, soft application feeling and high safety. That is, for realizing the pigments and extender pigments having extremely smooth tactile feeling and affinity to the skin and hair (biocompatibility), it is crucial to coat the pigments and extender pigments with an acylated amino acid mixture, wherein the amino acid may be in the salt form, such as polyvalent metal salt, obtained on acylating at least 14 amino acids obtained in turn on total hydrolysis of the animal protein such as silk and pearl, and plant protein such as wheat and soybeans.

EXAMPLES

The present invention is explained in further detail with reference to the following Examples and Comparative Examples. In the compositions shown in tables, the numerical values denote weight parts, unless otherwise specified.

Example 1-1
(Preparation of Coated Pigments and Extender Pigments-1)

To 100 parts by weight of sericite and 1000 parts by weight of pure water, 5 parts by weight in the solid content of an aqueous solution of sodium N-lauroyl silk amino acid salt (manufactured by PHYTOCOS, France) were added and stirred. To the resulting mass, a 1N aqueous solution of aluminum chloride was added dropwise. After adjusting the pH value to 4.0, and then under the pH value of 4.0 agitation was continued for 60 minutes, filtered, washed with water and dried at 115° C. for 12 hours. The resulting mass was pulverized to sericite coated with N-lauroyl silk amino acid aluminum. The coating (amounts of N-lauroyl silk amino acid aluminum for the coating layer) was in the 5 wt % to the sericite employed.

Meanwhile, in place of the aqueous solution of sodium N-lauroyl silk amino acid salt, an aqueous solution of 14 N-lauroyl amino acids sodium salt, which has the same composition and same concentration as the aqueous solution of sodium N-lauroyl silk amino acid salt above with respect to the 14 amino acids salts, obtained from the only 14 amino acids composition having the same composition and concentration as the above silk amino acid (see Table 1) only with respect to 14 amino acids, namely glycine, L-alanine, L-valine, L-leucine, L-isoleucine, L-phenylalanine, L-proline, L-threonine, L-serine, L-arginine, L-histidine, L-lysine, L-aspartic acid and L-glutamic acid, were prepared, and the processing similar to that described above was carried out as described above, and sericite coated with N-lauroyl-14 amino acids aluminum was prepared in the same way as in Example 1-1 above. The coating (amounts of N-lauroyl silk amino acid aluminum for the coating layer) was in the 5 wt % to the sericite employed. This coated pigments and extender pigments exhibited the product quality substantially comparable to the sericite coated with the silk amino acid as obtained above with respect to the points of evaluation discussed hereinbelow.

Example 1-2
(Preparation of Coated Pigments and Extender Pigments-2)
N-lauroyl silk amino acid aluminum coated talc was produced in the same way as in Example 1-1 except using talc in place of sericite in Example 1-1.

Example 1-3
(Preparation of Coated Pigments and Extender Pigments-3)
N-lauroyl silk amino acid aluminum coated mica was produced in the same way as in Example 1-1 except using mica in place of sericite in Example 1-1.

Example 1-4
(Preparation of Coated Pigments and Extender Pigments-4)
N-lauroyl silk amino acid aluminum coated titanium dioxide was produced in the same way as in Example 1-1 except using titanium dioxide in place of sericite in Example 1-1.

Example 1-5
(Preparation of Coated Pigments and Extender Pigments-5)
N-lauroyl silk amino acid aluminum coated yellow iron oxide was produced in the same way as in Example 1-1 except using yellow iron oxide in place of sericite in Example 1-1.

Example 1-6
(Preparation of Coated Pigments and Extender Pigments-6)
N-lauroyl silk amino acid aluminum coated red iron oxide was produced in the same way as in Example 1-1 except using red iron oxide in place of sericite in Example 1-1.

Example 1-7
(Preparation of Coated Pigments and Extender Pigments-7)
N-lauroyl silk amino acid aluminum coated black iron oxide was produced in the same way as in Example 1-1 except using black iron oxide in place of sericite in Example 1-1.

Example 1-8
(Preparation of Coated Pigments and Extender Pigments-8)
N-lauroyl silk amino acid aluminum coated mica titanium was produced in the same way as in Example 1-1 except using mica titanium (titanium-coated mica) in place of sericite in Example 1-1.

Example 1-9
(Preparation of Coated Pigments and Extender Pigments-9)
N-lauroyl silk amino acid aluminum coated silica beads was produced in the same way as in Example 1-1 except using silica beads in place of sericite in Example 1-1.

Example 2-1
(Preparation of Coated Pigments and Extender Pigments-10)
To 100 parts by weight of sericite and 1000 parts by weight of pure water, 5 parts by weight of paste-like N-caproyl silk amino acid (manufactured by PHYTOCOS, France) was added, stirred and dissolved. To the resulting solution was added a 1N-aqueous solution of sodium hydroxide dropwise for neutralization. To the resulting solution was added a 1N-aqueous solution of magnesium sulfate dropwise to adjust the pH value to 4.0. To the resulting solution was added a 1N-aqueous solution of magnesium sulfate dropwise to adjust its pH to 4.0. Under the pH value of 4.0, the resulting solution was agitated for 60 minutes, filtered, washed with water and dried at 115° C. for 12 hours. The resulting mass was pulverized to give N-caproyl silk amino acid magnesium coated sericite.

Example 2-2
(Preparation of Coated Pigments and Extender Pigments-11)
N-caproyl silk amino acid magnesium coated talc was produced in the same way as in Example 2-1 except using talc in place of sericite in Example 2-1.

Example 2-3
(Preparation of Coated Pigments and Extender Pigments-12)
N-caproyl silk amino acid magnesium coated mica was produced in the same way as in Example 2-1 except using mica in place of sericite in Example 2-1.

Example 2-4
(Preparation of Coated Pigments and Extender Pigments-13)
N-caproyl silk amino acid magnesium coated titanium dioxide was produced in the same way as in Example 2-1 except using titanium dioxide in place of sericite in Example 2-1.

Example 2-5
(Preparation of Coated Pigments and Extender Pigments-14)
N-caproyl silk amino acid magnesium coated yellow iron oxide was produced in the same way as in Example 2-1 except using yellow iron oxide in place of sericite in Example 2-1.

Example 2-6
(Preparation of Coated Pigments and Extender Pigments-15)
N-caproyl silk amino acid magnesium coated red iron oxide was produced in the same way as in Example 2-1 except using red iron oxide in place of sericite in Example 2-1.

Example 2-7
(Preparation of Coated Pigments and Extender Pigments-16)

N-caproyl silk amino acid magnesium coated black iron oxide was produced in the same way as in Example 2-1 except using black iron oxide in place of sericite in Example 2-1.

Example 2-8
(Preparation of Coated Pigments and Extender Pigments-17)

N-caproyl silk amino acid magnesium coated mica titanium was produced in the same way as in Example 2-1 except using mica titanium (titanium-coated mica) in place of sericite in Example 2-1.

Example 2-9
(Preparation of Coated Pigments and Extender Pigments-18)

N-caproyl silk amino acid magnesium coated silica beads was produced in the same way as in Example 2-1 except using silica beads in place of sericite in Example 2-1.

Example 3-1
(Preparation of Coated Pigments and Extender Pigments-19)

To 100 parts by weight of sericite and 1000 parts by weight of pure water, 5 parts by weight in the solid content of solid powdered N-palmitoyl silk amino acid, manufactured by PHYTOCOS, France, was added and heated to 60° C. and added to dropwise with a 1N-aqueous sodium hydroxide solution for neutralization. To the resulting solution was added dropwise a 1N-aqueous solution of zinc sulfate to adjust the pH value to 4.0. Under the pH value of 4.0 the resulting mass was stirred for 60 minutes, filtered, washed with water and dried at 115° C. for 12 hours. The resulting mass was pulverized to give N-palmitoyl silk amino acid zinc coated sericite.

Example 3-2
(Preparation of Coated Pigments and Extender Pigments-20)

N-palmitoyl silk amino acid zinc coated talc was produced in the same way as in Example 3-1 except using talc in place of sericite in Example 3-1.

Example 3-3
(Preparation of Coated Pigments and Extender Pigments-21)

N-palmitoyl silk amino acid zinc coated mica was produced in the same way as in Example 3-1 except using mica in place of sericite in Example 3-1.

Example 3-4
(Preparation of Coated Pigments and Extender Pigments-22)

N-palmitoyl silk amino acid zinc coated titanium dioxide was produced in the same way as in Example 3-1 except using titanium dioxide in place of sericite in Example 3-1.

Example 3-5
(Preparation of Coated Pigments and Extender Pigments-23)

N-palmitoyl silk amino acid zinc coated yellow iron oxide was produced in the same way as in Example 3-1 except using yellow iron oxide in place of sericite in Example 3-1.

Example 3-6
(Preparation of Coated Pigments and Extender Pigments-24)

N-palmitoyl silk amino acid zinc coated red iron oxide was produced in the same way as in Example 3-1 except using red iron oxide in place of sericite in Example 3-1.

Example 3-7
(Preparation of Coated Pigments and Extender Pigments-25)

N-palmitoyl silk amino acid zinc coated black iron oxide was produced in the same way as in Example 3-1 except using black iron oxide in place of sericite in Example 3-1.

Example 3-8
(Preparation of Coated Pigments and Extender Pigments-26)

N-palmitoyl silk amino acid zinc coated mica titanium was produced in the same way as in Example 3-1 except using mica titanium in place of sericite in Example 3-1.

Example 3-9
(Preparation of Coated Pigments and Extender Pigments-27)

N-palmitoyl silk amino acid zinc coated silica beads was produced in the same way as in Example 3-1 except using silica beads in place of sericite in Example 3-1.

Example 4-1
(Preparation of Coated Pigments and Extender Pigments-28)

To 100 parts by weight of sericite and 1000 parts by weight of pure water, 5 parts by weight of solid powdered N-palmitoyl pearl amino acid is added and heated to 60° C. To this solution added dropwise a 1N-aqueous sodium hydroxide solution for neutralization. To the resulting solution was added dropwise a 1N-aqueous solution of aluminum sulfate to adjust the pH value to 4.0. Under the pH value of 4.0, the resulting mass was stirred for 60 minutes, filtered, washed with water and dried at 115° C. for 12 hours. The resulting mass was pulverized to give N-palmitoyl pearl amino acid aluminum coated sericite.

Example 4-2
(Preparation of Coated Pigments and Extender Pigments-29)

N-palmitoyl pearl amino acid aluminum coated talc was produced in the same way as in Example 4-1 except using talc in place of sericite in Example 4-1.

Example 4-3
(Preparation of Coated Pigments and Extender Pigments-30)

N-palmitoyl pearl amino acid aluminum coated mica was produced in the same way as in Example 4-1 except using mica in place of sericite in Example 4-1.

Example 4-4
(Preparation of Coated Pigments and Extender Pigments-31)

N-palmitoyl pearl amino acid aluminum coated titanium dioxide was produced in the same way as in Example 4-1 except using titanium dioxide in place of sericite in Example 4-1.

Example 4-5
(Preparation of Coated Pigments and Extender Pigments-32)

N-palmitoyl pearl amino acid aluminum coated yellow iron oxide was produced in the same way as in Example 4-1 except using yellow iron oxide in place of sericite in Example 4-1.

Example 4-6
(Preparation of Coated Pigments and Extender Pigments-33)

N-palmitoyl pearl amino acid aluminum coated red iron oxide was produced in the same way as in Example 4-1 except using red iron oxide in place of sericite in Example 4-1.

Example 4-7
(Preparation of Coated Pigments and Extender Pigments-34)

N-palmitoyl pearl amino acid aluminum coated black iron oxide was produced in the same way as in Example 4-1 except using black iron oxide in place of sericite in Example 4-1.

Example 4-8
(Preparation of Coated Pigments and Extender Pigments-35)

N-palmitoyl pearl amino acid aluminum coated mica titanium was produced in the same way as in Example 4-1 except using mica titanium in place of sericite in Example 4-1.

Example 4-9
(Preparation of Coated Pigments and Extender Pigments-36)

N-palmitoyl pearl amino acid aluminum coated silica beads was produced in the same way as in Example 4-1 except using silica beads in place of sericite in Example 4-1.

Example 5-1
(Preparation of Coated Pigments and Extender Pigments-37)

To 100 parts by weight of sericite and 1000 parts by weight of pure water, 5 parts by weight in the solid content of solid powdered N-palmitoyl soybean amino acid, was added and heated to 60° C. To the resulting solution was added dropwise a 1N-aqueous sodium hydroxide solution for neutralization. To the resulting solution was added dropwise a 1N-aqueous solution of aluminum chloride and stirred for 60 minutes with the pH value of 4.0. The resulting mass was filtered, washed with water, dried at 115° C. for 12 hours and pulverized to give N-palmitoyl soybean amino acid aluminum coated sericite.

Example 5-2
(Preparation of Coated Pigments and Extender Pigments-38)

N-palmitoyl soybean amino acid aluminum coated talc was produced in the same way as in Example 5-1 except using talc in place of sericite in Example 5-1.

Example 5-3
(Preparation of Coated Pigments and Extender Pigments-39)

N-palmitoyl soybean amino acid aluminum coated mica was produced in the same way as in Example 5-1 except using mica in place of sericite in Example 5-1.

Example 5-4
(Preparation of Coated Pigments and Extender Pigments-40)

N-palmitoyl soybean amino acid aluminum coated titanium dioxide was produced in the same way as in Example 5-1 except using titanium dioxide in place of sericite in Example 5-1.

Example 5-5
(Preparation of Coated Pigments and Extender Pigments-41)

N-palmitoyl soybean amino acid aluminum coated yellow iron oxide was produced in the same way as in Example 5-1 except using yellow iron oxide in place of sericite in Example 5-1.

Example 5-6
(Preparation of Coated Pigments and Extender Pigments-42)

N-palmitoyl soybean amino acid aluminum coated red iron oxide was produced in the same way as in Example 5-1 except using red iron oxide in place of sericite in Example 5-1.

Example 5-7
(Preparation of Coated Pigments and Extender Pigments-43)

N-palmitoyl soybean amino acid aluminum coated black iron oxide was produced in the same way as in Example 5-1 except using black iron oxide in place of sericite in Example 5-1.

Example 5-8
(Preparation of Coated Pigments and Extender Pigments-44)

N-palmitoyl soybean amino acid aluminum coated mica titanium was produced in the same way as in Example 5-1 except using mica titanium in place of sericite in Example 5-1.

Example 5-9
(Preparation of Coated Pigments and Extender Pigments-45)

N-palmitoyl soybean amino acid aluminum coated silica beads was produced in the same way as in Example 5-1 except using silica beads in place of sericite in Example 5-1.

Example 6-1
(Preparation of Coated Pigments and Extender Pigments-46

To 100 parts by weight of sericite and 1000 parts by weight of pure water, 5 parts by weight in the solid content of solid powdered N-lauroyl wheat amino acid potassium salt (amino-form manufactured by Croda, Japan) were added and heated to 60° C. To the resulting solution was added dropwise a 1N aqueous solution of zinc acetate and stirred for 60 minutes with the pH value adjusted to 4.0. The resulting mass was filtered, washed with water, dried at 115° C. for 12 hours and pulverized to N-lauroyl wheat amino acid zinc coated sericite.

Example 6-2
(Preparation of Coated Pigments and Extender Pigments-47)

N-lauroyl wheat amino acid zinc coated talc was produced in the same way as in Example 6-1 except using talc in place of sericite in Example 6-1.

Example 6-3
(Preparation of Coated Pigments and Extender Pigments-48)

N-lauroyl wheat amino acid zinc coated mica was produced in the same way as in Example 6-1 except using mica in place of sericite in Example 6-1.

Example 6-4
(Preparation of Coated Pigments and Extender Pigments-49)

N-lauroyl wheat amino acid zinc coated titanium dioxide was produced in the same way as in Example 6-1 except using titanium dioxide in place of sericite in Example 6-1.

Example 6-5
(Preparation of Coated Pigments and Extender Pigments-50)

N-lauroyl wheat amino acid zinc coated yellow iron oxide was produced in the same way as in Example 6-1 except using yellow iron oxide in place of sericite in Example 6-1.

Example 6-6
(Preparation of Coated Pigments and Extender Pigments-51)

N-lauroyl wheat amino acid zinc coated red iron oxide was produced in the same way as in Example 6-1 except using red iron oxide in place of sericite in Example 6-1.

Example 6-7
(Preparation of Coated Pigments and Extender Pigments-52)

N-lauroyl wheat amino acid zinc coated black iron oxide was produced in the same way as in Example 6-1 except using black iron oxide in place of sericite in Example 6-1.

Example 6-8
(Preparation of Coated Pigments and Extender Pigments-53)

N-lauroyl wheat amino acid zinc coated mica titanium was produced in the same way as in Example 6-1 except using mica titanium in place of sericite in Example 6-1.

Example 6-9
(Preparation of Coated Pigments and Extender Pigments-54)

N-lauroyl wheat amino acid zinc coated silica beads were produced in the same way as in Example 6-1 except using silica beads in place of sericite in Example 6-1.

Example 7-1
(Preparation of Coated Pigments and Extender Pigments-55)

To 100 parts by weight of sericite and 1000 parts by weight of pure water, 2.5 parts by weight each in the solid contents of powdered N-lauroyl wheat amino acid and N-stearoyl soybean amino acid were added and heated to 60° C. To the resulting mass was added dropwise a 1N aqueous solution of sodium hydroxide for neutralization. To the resulting solution was added dropwise a 1N aqueous solution of calcium acetate to adjust the pH to 4.0. Under the pH value of 4.0, the resulting mass was stirred for 60 minutes, filtered, washed with water and dried at 115° C. for 12 hours. The dried product was then pulverized to sericite coated with N-lauroyl wheat amino acid calcium salt and N-stearoyl soybean amino acid calcium salt.

Example 7-2
(Preparation of Coated Pigments and Extender Pigments-56)

The talc coated with N-lauroyl wheat amino acid calcium and N-stearoyl soybean amino acid calcium was prepared in the same way as in Example 7-1 except using talc in place of sericite in Example 7-1.

Example 7-3
(Preparation of Coated Pigments and Extender Pigments-57)

The mica coated with N-lauroyl wheat amino acid calcium and N-stearoyl soybean amino acid calcium was prepared in the same way as in Example 7-1 except using mica in place of sericite in Example 7-1.

Example 7-4
(Preparation of Coated Pigments and Extender Pigments-58)

The titanium dioxide coated with N-lauroyl wheat amino acid calcium and N-stearoyl soybean amino acid calcium was prepared in the same way as in Example 7-1 except using titanium dioxide in place of sericite in Example 7-1.

Example 7-5
(Preparation of Coated Pigments and Extender Pigments-59)

The yellow iron oxide coated with N-lauroyl wheat amino acid calcium and N-stearoyl soybean amino acid calcium was prepared in the same way as in Example 7-1 except using yellow iron oxide in place of sericite in Example 7-1.

Example 7-6
(Preparation of Coated Pigments and Extender Pigments-60)

The red iron oxide coated with N-lauroyl wheat amino acid calcium and N-stearoyl soybean amino acid calcium was prepared in the same way as in Example 7-1 except using red iron oxide in place of sericite in Example 7-1.

Example 7-7
(Preparation of Coated Pigments and Extender Pigments-61)

The black iron oxide coated with N-lauroyl wheat amino acid calcium and N-stearoyl soybean amino acid calcium was prepared in the same way as in Example 7-1 except using black iron oxide in place of sericite in Example 7-1.

Example 7-8
(Preparation of Coated Pigments and Extender Pigments-62)

The mica titanium coated with N-lauroyl wheat amino acid calcium and N-stearoyl soybean amino acid calcium was prepared in the same way as in Example 7-1 except using mica titanium in place of sericite in Example 7-1.

Example 7-9
(Preparation of Coated Pigments and Extender Pigments-63)

The silica beads coated with N-lauroyl wheat amino acid calcium and N-stearoyl soybean amino acid calcium was prepared in the same way as in Example 7-1 except using silica beads in place of sericite in Example 7-1.

Meanwhile, in all the products of coated pigments and extender pigments obtained in Examples 1-2 to 7-9 above, the coating layer was in the 5 wt % to the pigments and extender pigments as the starting material.

Comparative Example 1-1
(Preparation of Coated Pigments and Extender Pigments-64)

Sericite was surface-treated by a method described in Example 1(1) of JP Patent Kokoku Publication JP-B-1-50202 to give sericite coated with aluminium N-myristoyl-L-glutamate (surface coating quantity, 5 wt %).

Comparative Example 1-2
(Preparation of Coated Pigments and Extender Pigments-65)

The talc processed with aluminum N-myristoyl-L-glutamate (surface coating quantity, 5 wt %) was obtained in the same way as in Comparative Example 1-1 except using talc in place of sericite in Comparative Example 1-1.

Comparative Example 1-3
(Preparation of Coated Pigments and Extender Pigments-66)

The mica processed with aluminium N-myristoyl-L-glutamate (surface coating quantity, 5 wt %) was obtained in the same way as in Comparative Example 1-1 except using mica in place of sericite in Comparative Example 1-1.

Comparative Example 1-4
(Preparation of Coated Pigments and Extender Pigments-67)

The titanium dioxide processed with aluminium N-myristoyl-L-glutamate (surface coating quantity, 5 wt %) was obtained in the same way as in Comparative Example 1-1 except using titanium dioxide in place of sericite in Comparative Example 1-1.

Comparative Example 1-5
(Preparation of Coated Pigments and Extender Pigments-68)

The yellow iron oxide processed with aluminium N-myristoyl-L-glutamate (surface coating quantity, 5 wt %) was obtained in the same way as in Comparative Example 1-1 except using yellow iron oxide in place of sericite in Comparative Example 1-1.

Comparative Example 1-6
(Preparation of Coated Pigments and Extender Pigments-69)

The red iron oxide processed with aluminium N-myristoyl-L-glutamate (surface coating quantity, 5 wt %) was obtained in the same way as in Comparative Example 1-1 except using red iron oxide in place of sericite in Comparative Example 1-1.

Comparative Example 1-7
(Preparation of Coated Pigments and Extender Pigments-70)

The black iron oxide processed with aluminium N-myristoyl-L-glutamate (surface coating quantity, 5 wt %) was obtained in the same way as in Comparative Example 1-1 except using black iron oxide in place of sericite in Comparative Example 1-1.

Comparative Example 1-8
(Preparation of Coated Pigments and Extender Pigments-71)

The mica titanium processed with aluminium N-myristoyl-L-glutamate (surface coating quantity, 5 wt %) was obtained in the same way as in Comparative Example 1-1 except using mica titanium in place of sericite in Comparative Example 1-1.

Comparative Example 1-9
(Preparation of Coated Pigments and Extender Pigments-72)

The silica beads processed with aluminium N-myristoyl-L-glutamate (surface coating quantity, 5 wt %) was obtained in the same way as in Comparative Example 1-1 except using silica beads in place of sericite in Comparative Example 1-1.

Comparative Example 2-1
(Preparation of Coated Pigments and Extender Pigments-73)

Sericite was surface-treated by a method described in Example 2 of JP Patent Kokai Publication JP-A-61-7207 to give sericite treated with N-lauroyl lysine (surface coating quantity, 5 wt %).

Comparative Example 2-2
(Preparation of Coated Pigments and Extender Pigments-74)

The talc processed with N-lauroyl lysine (surface coating quantity, 5 wt %) was obtained in the same way as in Comparative Example 2-1 except using talc in place of sericite in Comparative Example 2-1.

Comparative Example 2-3
(Preparation of Coated Pigments and Extender Pigments-75)

The mica processed with N-lauroyl lysine (surface coating quantity, 5 wt %) was obtained in the same way as in Comparative Example 2-1 except using mica in place of sericite in Comparative Example 2-1.

Comparative Example 2-4
(Preparation of Coated Pigments and Extender Pigments-76)

The titanium dioxide processed with N-lauroyl lysine (surface coating quantity, 5 wt %) was obtained in the same way as in Comparative Example 2-1 except using titanium dioxide in place of sericite in Comparative Example 2-1.

Comparative Example 2-5
(Preparation of Coated Pigments and Extender Pigments-77)

The yellow iron oxide processed with N-lauroyl lysine (surface coating quantity, 5 wt %) was obtained in the same way as in Comparative Example 2-1 except using yellow iron oxide in place of sericite in Comparative Example 2-1.

Comparative Example 2-6
(Preparation of Coated Pigments and Extender Pigments-78)

The red iron oxide processed with N-lauroyl lysine (surface coating quantity, 5 wt %) was obtained in the same way as in Comparative Example 2-1 except using red iron oxide in place of sericite in Comparative Example 2-1.

Comparative Example 2-7
(Preparation of Coated Pigments and Extender Pigments-79)

The black iron oxide processed with N-lauroyl lysine (surface coating quantity, 5 wt %) was obtained in the same way as in Comparative Example 2-1 except using black iron oxide in place of sericite in Comparative Example 2-1.

Comparative Example 2-8
(Preparation of Coated Pigments and Extender Pigments-80)

The mica titanium processed with N-lauroyl lysine (surface coating quantity, 5 wt %) was obtained in the same way as in Comparative Example 2-1 except using mica titanium in place of sericite in Comparative Example 2-1.

Comparative Example 2-9
(Preparation of Coated Pigments and Extender Pigments-81)

The silica beads processed with N-lauroyl lysine (surface coating quantity, 5 wt %) was obtained in the same way as in Comparative Example 2-1 except using silica beads in place of sericite in Comparative Example 2-1.

Comparative Example 3-1
(Preparation of Coated Pigments and Extender Pigments-82)

Sericite was surface-treated by a method described in Example 1 of JP Patent Kokai Publication JP-A-9-328413 to give sericite treated with lauroyl hydrolyzed silk peptide (surface coating quantity, 5 wt %).

Comparative Example 3-2
(Preparation of Coated Pigments and Extender Pigments-83)

The talc processed with lauroyl hydrolyzed silk peptide (surface coating quantity, 5 wt %) was obtained in the same way as in Comparative Example 3-1 except using talc in place of sericite in Comparative Example 3-1.

Comparative Example 3-3
(Preparation of Coated Pigments and Extender Pigments-84)

The mica processed with lauroyl hydrolyzed silk peptide (surface coating quantity, 5 wt %) was obtained in the same way as in Comparative Example 3-1 except using mica in place of sericite in Comparative Example 3-1.

Comparative Example 3-4
(Preparation of Coated Pigments and Extender Pigments-85)

The titanium dioxide processed with lauroyl hydrolyzed silk peptide (surface coating quantity, 5 wt %) was obtained in the same way as in Comparative Example 3-1 except using titanium dioxide in place of sericite in Comparative Example 3-1.

Comparative Example 3-5
(Preparation of Coated Pigments and Extender Pigments-86)

The yellow iron oxide processed with lauroyl hydrolyzed silk peptide (surface coating quantity, 5 wt %) was obtained in the same way as in Comparative Example 3-1 except using yellow iron oxide in place of sericite in Comparative Example 3-1.

Comparative Example 3-6
(Preparation of Coated Pigments and Extender Pigments-87)

The red iron oxide processed with lauroyl hydrolyzed silk peptide (surface coating quantity, 5 wt %) was obtained in the same way as in Comparative Example 3-1 except using red iron oxide in place of sericite in Comparative Example 3-1.

Comparative Example 3-7
(Preparation of Coated Pigments and Extender Pigments-88)

The black iron oxide processed with lauroyl hydrolyzed silk peptide (surface coating quantity, 5 wt %) was obtained in the same way as in Comparative Example 3-1 except using black iron oxide in place of sericite in Comparative Example 3-1.

Comparative Example 3-8
(Preparation of Coated Pigments and Extender Pigments-89)

The mica titanium processed with lauroyl hydrolyzed silk peptide (surface coating quantity, 5 wt %) was obtained in the same way as in Comparative Example 3-1 except using mica titanium in place of sericite in Comparative Example 3-1.

Comparative Example 3-9
(Preparation of Coated Pigments and Extender Pigments-90)

The silica beads processed with lauroyl hydrolyzed silk peptide (surface coating quantity, 5 wt %) was obtained in the same way as in Comparative Example 3-1 except using silica beads in place of sericite in Comparative Example 3-1.

Comparative Example 4-1
(Preparation of Coated Pigments and Extender Pigments-91)

Sericite was surface-treated by a method described in Example 3 of Japanese Patent Kokai Publication JP-A-10-226626 to give sericite surface-treated with sericine (surface coating quantity, 5 wt %).

Comparative Example 4-2
(Preparation of Coated Pigments and Extender Pigments-92)

The talc processed with sericine (surface coating quantity, 5 wt %) was obtained in the same way as in Comparative Example 4-1 except using talc in place of sericite in Comparative Example 4-1.

Comparative Example 4-3
(Preparation of Coated Pigments and Extender Pigments-93)

The mica processed with sericine (surface coating quantity, 5 wt %) was obtained in the same way as in Comparative Example 4-1 except using mica in place of sericite in Comparative Example 4-1.

Comparative Example 4-4
(Preparation of Coated Pigments and Extender Pigments-94)

The titanium dioxide processed with sericine (surface coating quantity, 5 wt %) was obtained in the same way as in Comparative Example 4-1 except using titanium dioxide in place of sericite in Comparative Example 4-1.

Comparative Example 4-5
(Preparation of Coated Pigments and Extender Pigments-95)

The yellow iron oxide processed with sericine (surface coating quantity, 5 wt %) was obtained in the same way as in Comparative Example 4-1 except using yellow iron oxide in place of sericite in Comparative Example 4-1.

Comparative Example 4-6
(Preparation of Coated Pigments and Extender Pigments-96)

The red iron oxide processed with sericine (surface coating quantity, 5 wt %) was obtained in the same way as in Comparative Example 4-1 except using red iron oxide in place of sericite in Comparative Example 4-1.

Comparative Example 4-7
(Preparation of Coated Pigments and Extender Pigments-97)

The black iron oxide processed with sericine (surface coating quantity, 5 wt %) was obtained in the same way as in Comparative Example 4-1 except using black iron oxide in place of sericite in Comparative Example 4-1.

Comparative Example 4-8
(Preparation of Coated Pigments and Extender Pigments-98)

The mica titanium processed with sericine (surface coating quantity, 5 wt %) was obtained in the same way as in Comparative Example 4-1 except using mica titanium in place of sericite in Comparative Example 4-1.

Comparative Example 4-9
(Preparation of Coated Pigments and Extender Pigments-99)

The silica beads processed with sericine (surface coating quantity, 5 wt %) were obtained in the same way as in Comparative Example 4-1 except using silica beads in place of sericite in Comparative Example 4-1.

Comparative Example 5-1
(Preparation of Coated Pigments and Extender Pigments-100)

To 100 parts by weight of sericite and 1000 parts by weight of pure water, 2 parts by weight of N-stearoyl-N-methyl alanine sodium stated in Japanese Patent Kokoku Publication JP-B-1-50202, 1.5 parts by weight of disodium N-stearoyl-L-glutamate and 1.5 parts by weight of monosodium N-lauroyl-L-aspartate stated in Japanese Patent Kokai Publication JP-A-3-200879 and stirred. To the resulting mass was added dropwise a 1N aqueous solution of aluminum nitrate. With the pH value adjusted to 4.0, the resulting mass was stirred for 60 minutes, filtered, washed with water and dried at 115° C. for 12 hours. The resulting mass was pulverized to sericite coated with a mixture of three different acylated amino acids, namely sericite coated with N-stearoyl-N-methyl alanine aluminum, aluminium N-stearoyl-L-glutamate and aluminium N-lauroyl-L-aspartate (surface coating quantity, 5 wt %).

Comparative Example 5-2
(Preparation of Coated Pigments and Extender Pigments-101)

The talc coated with three acylated amino acids, namely talc coated with N-stearoyl-N-methyl alanine aluminum, aluminium N-stearoyl-L-glutamate and aluminium N-lauroyl-L-aspartate (surface coating quantity, 5 wt %) was prepared in the same way as in Comparative Example 5-1 except using talc in place of sericite in Comparative Example 5-1.

Comparative Example 5-3
(Preparation of Coated Pigments and Extender Pigments-102)

The mica coated with three acylated amino acids, namely sericite coated with N-stearoyl-N-methyl alanine aluminum, aluminium N-stearoyl-L-glutamate and aluminium N-lauroyl-L-aspartate (surface coating quantity, 5 wt %) was prepared in the same way as in Comparative Example 5-1 except using mica in place of sericite in Comparative Example 5-1.

Comparative Example 5-4
(Preparation of Coated Pigments and Extender Pigments-103)

The titanium dioxide coated with three acylated amino acids, namely titanium dioxide coated with N-stearoyl-N-methyl alanine aluminium, aluminium N-stearoyl-L-glutamate and aluminium N-lauroyl-L-aspartate (surface coating quantity, 5 wt %) was prepared in the same way as in Comparative Example 5-1 except using titanium dioxide in place of sericite in Comparative Example 5-1.

Comparative Example 5-5
(Preparation of Coated Pigments and Extender Pigments-104)

The yellow iron oxide coated with three acylated amino acids, namely yellow iron oxide coated with N-stearoyl-N-methyl alanine aluminium, aluminium N-stearoyl-L-glutamate and aluminium N-lauroyl-L-aspartate (surface coating quantity, 5 wt %) was prepared in the same way as in Comparative Example 5-1 except using yellow iron oxide in place of sericite in Comparative Example 5-1.

Comparative Example 5-6
(Preparation of Coated Pigments and Extender Pigments-105)

The red iron oxide coated with three acylated amino acids, namely red iron oxide coated with N-stearoyl-N-methyl alanine aluminium, aluminium N-stearoyl-L-glutamate and aluminum N-lauroyl-L-aspartate (surface coating quantity, 5 wt %) was prepared in the same way as in Comparative Example 5-1 except using red iron oxide in place of sericite in Comparative Example 5-1.

Comparative Example 5-7
(Preparation of Coated Pigments and Extender Pigments-106)

The black iron oxide coated with three acylated amino acids, namely black iron oxide coated with N-stearoyl-N-methyl alanine aluminium, aluminium N-stearoyl-L-glutamate and aluminium N-lauroyl-L-aspartate (surface coating quantity, 5 wt %) was prepared in the same way as in Comparative Example 5-1 except using black iron oxide in place of sericite in Comparative Example 5-1.

Comparative Example 5-8
(Preparation of Coated Pigments and Extender Pigments-107)

The mica titanium coated with three acylated amino acids, namely mica titanium coated with N-stearoyl-N-methyl alanine aluminium, aluminium N-stearoyl-L-glutamate and aluminium N-lauroyl-L-aspartate (surface coating quantity, 5 wt %) was prepared in the same way as in Comparative Example 5-1 except using mica titanium in place of sericite in Comparative Example 5-1.

Comparative Example 5-9
(Preparation of Coated Pigments and Extender Pigments-108)

The silica beads coated with three acylated amino acids, namely silica beads coated with N-stearoyl-N-methyl alanine aluminium, aluminium N-stearoyl-L-glutamate and aluminium N-lauroyl-L-aspartate (surface coating quantity, 5 wt %) was prepared in the same way as in Comparative Example 5-1 except using silica beads in place of sericite in Comparative Example 5-1.

The coated pigments and extender pigments of the present invention, obtained as described above, and the coated pigments and extender pigments of the Comparative Example, processed by a known conventional method, were evaluated by the following testing method.

Test on Smoothness of Pigments and Extender Pigments

The pigments and extender pigments was applied on a 8 cm by 5 cm collagen paper sheet manufactured by IDEMITSU KAGAKU under the trade name of "SUPPLALE" at a amount of 1 mg/cm$^2$, and set on a reciprocating friction coefficient measurement tester manufactured by KATO-TEC. A non-coated collagen sheet was set and placed under a load of 50 g/cm$^2$. The resulting assembly was reciprocated five times to plot changes in the friction coefficient (MIU) in a graph. Tests on smoothness was conducted on sericite representing most significant difference in smoothness.

Figure 1:
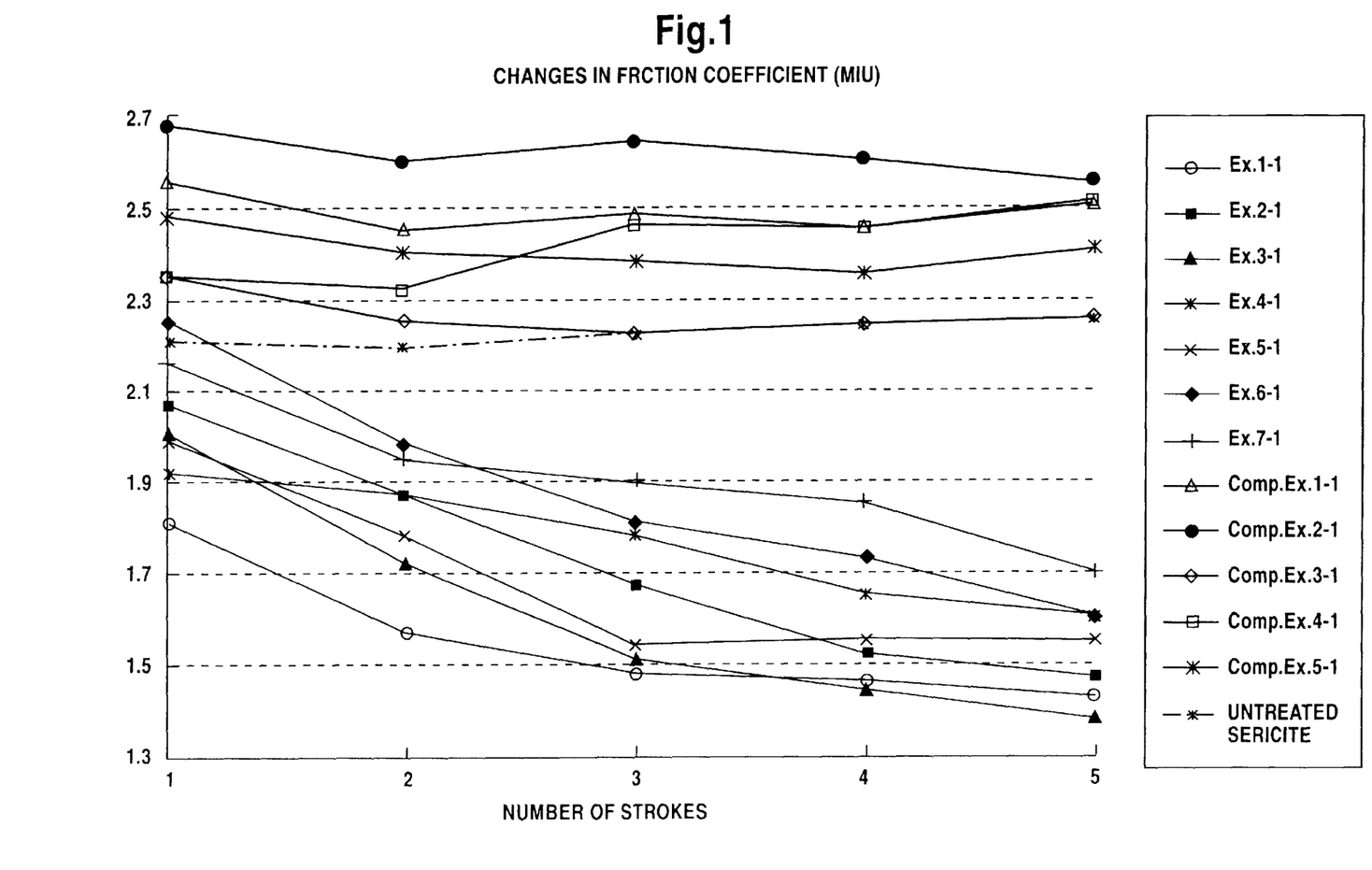
FIG. 1 shows the results of tests on smoothness of the pigments and extender pigments in the present invention.

FIG. 1 shows the results of the test on smoothness of the pigments and extender pigments.

As may be seen from FIG. 1, the inventive coated pigments and extender pigments of Examples 1 to 7 in the present invention are low in the friction coefficient and excellent in smoothness (smooth tactile feeling). Also, the pigments and extender pigments in the present invention is superior to the non-coated, sericite, that is, non-processed sericite.

The coated pigments and extender pigments in the present invention was processed into face powders of the following simple composition which were then evaluated by a panel consisting of thirty people as to affinity to the skin in accordance with the following standards. Meanwhile, affinity to the skin was checked as to four items of spreadability, smoothness on application, moist feeling and application feeling after application.

(Evaluation points)

excellent 4 points
good 3 points
acceptable 2 points
poor 1 point
very poor 0 point (Judgment)

average point of 3.0 to 4.0 ⊚
average point of 2.0 to 3.0 ○
average point of 1.0 to 2.0 Δ
average point of 0 to 1.0 X (Composition of face powders)

1. mica of Ex. 1 to 7 or Comp. Ex. 1 to 5 79 parts
2. talc of Ex. 1 to 7 or Comp. Ex. 1 to 5 15 parts
3. squalane 6 parts (Manufacturing method)

The mica of above component 1. and the talc of the above component 2. are mixed together and passed through a pulverizer. The obtained mixture is moved to a high-speed blender where the squalane of the above component 3. is added and mixed for five minutes. The resulting mass was passed through a 100-mesh sieve to produce face powders.

The results of evaluation by the panel are shown in Table 2.

TABLE 2

(Results of Tests on Affinity to Skin)

| Samples | Spreadability | Smoothness | Moist Feeling | Application feeling |
|---|---|---|---|---|
| Face powder of Ex. 1 | ⊚ | ⊚ | ⊚ | ⊚ |
| Face powder of Ex. 2 | ⊚ | ⊚ | ⊚ | ⊚ |
| Face powder of Ex. 3 | ⊚ | ⊚ | ⊚ | ⊚ |
| Face powder of Ex. 4 | ⊚ | ⊚ | ⊚ | ⊚ |
| Face powder of Ex. 5 | ⊚ | ⊚ | ○ | ⊚ |
| Face powder of Ex. 6 | ⊚ | ⊚ | ○ | ⊚ |
| Face powder of Ex. 7 | ⊚ | ⊚ | ⊚ | ⊚ |
| Face powder of Comp. Ex. 1 | Δ | Δ | x | x |
| Face powder of Comp. Ex. 2 | Δ | Δ | x | x |
| Face powder of Comp. Ex. 3 | x | x | Δ | Δ |
| Face powder of Comp. Ex. 4 | x | x | Δ | Δ |
| Face powder of Comp. Ex. 5 | Δ | Δ | Δ | Δ |

As may be seen from the results of Table 2, the face powders containing the coated pigments and extender pigments of Examples 1 to 7 in the present invention are superior in affinity to the skin.

The composition of pressed powders is shown in Table 3:

TABLE 3

| Composition | Ex. 8 (using processed particle of Ex. 1) | Comp. Ex. 6 (using processed particle of Comp. Ex. 1) | Comp. Ex. 7 (using processed particle of Comp. Ex. 2) |
|---|---|---|---|
| (1) talc | to 100.0*1 | Same as shown left | Same as shown left |
| (2) sericite | 12.0 | Same as shown left | Same as shown left |
| (3) titanium dioxide | 12.0 | Same as shown left | Same as shown left |
| (4) colored pigments | Proper amount | Same as shown left | same as shown left |
| (5) silica beads | 9.0 | Same as shown left | same as shown left |
| (6) cosmol43*2 | 8.9 | Same as shown left | same as shown left |
| (7) squalane | 2.0 | Same as shown left | same as shown left |
| (8) KF-96 (20 cs)*3 | 1.3 | Same as shown left | same as shown left |
| (9) perfume | Proper amount | Same as shown left | same as shown left |

*1(to 100.0) means that adjustment is to be made 100.0.
*2is triisostearic acid polyglyceryl manufactured by NISSHIN SEIYU KK.
*3 is dimethyl polysiloxane manufactured by SHIN-ETSU KAGAKU KK.

Manufacturing Method

After mixing (1) to (5) by a Henschel mixer, (6) to (9) were sprayed into the mixture to effect homogeneous mixing. The resulting mixture was pulverized by an atomizer and sieved and the resulting mass was compression-molded onto a saucer to produce pressed powders.

The pressed powders of the Comparative Examples 6 and 7 were heavy and powdery, whereas the pressed powder of Example 8 presented extremely smooth tactile feeling and optimum affinity.

The composition of two way foundation is shown in Table 4:

TABLE 4

| Composition | Ex. 9 (using processed particle of Ex. 2) | Comp. Ex. 8 (using processed particle of Comp. Ex. 3) | Comp. Ex. 9 (using processed particle of Comp. Ex. 4) |
|---|---|---|---|
| (1) talc | To 100.0 | Same as shown left | same as shown left |
| (2) sericite | 10.0 | Same as shown left | same as shown left |
| (3) mica | 4.5 | Same as shown left | same as shown left |
| (4) titanium dioxide | 7.0 | Same as shown left | same as shown left |
| (5) colored pigments | Proper amount | Same as shown left | same as shown left |
| (6) cover leaf PC-1035*1 | 6.0 | Same as shown left | same as shown left |
| (7) zinc stearate | 2.5 | Same as shown left | same as shown left |
| (8) PMMA*2 | 8.5 | same as shown left | same as shown left |
| (9) dimethyl polysiloxane (100 cs) | 4.5 | same as shown left | same as shown left |
| (10) squalane | 5.0 | same as shown left | same as shown left |
| (11) octyldodecyl oleate | 2.5 | same as shown left | same as shown left |
| (12) perfume | Proper amount | same as shown left | same as shown left |

*1is titanium dioxide coated sericite (manufactured by SHOKUBAI KASEI KOGYO KK).
*2is polymethyl methacrylate.

Manufacturing Method

After mixing (1) to (8) by a Henschel mixer, homogenized components (9) to (12) were added to the resulting mixture and mixed homogeneously. The resulting mixture was pulverized by an atomizer and sieved and the resulting mass was compression-molded onto a saucer to produce two way foundations.

The two way foundations of the Comparative Examples 8 and 9 were heavy and powdery, whereas the two way foundation of Example 9 presented extremely smooth tactile feeling and optimum affinity.

The composition of the powdered eye shadow is shown in Table 5:

TABLE 5

| Composition | Ex. 10 (using processed particle of Ex. 3) | Comp. Ex. 10 (using processed particle of Comp. Ex. 5) | Comp. Ex. 11 (using processed particle of Comp. Ex. 1) |
|---|---|---|---|
| (1) sericite | 25.0 | Same as shown left | same as shown left |
| (2) mica | 21.0 | Same as shown left | same as shown left |
| (3) mica titanium | 4.5 | Same as shown left | same as shown left |
| (4) colored pigments | 7.5 | Same as shown left | same as shown left |
| (5) silica beads | 8.7 | Same as shown Left | same as shown left |
| (6) dimethyl polysiloxane | 2.5 | same as shown left | same as shown left |
| (7) decamethylcyclopentasiloxane | 8.0 | same as shown left | same as shown left |
| (8) serecin wax | 3.5 | same as shown left | same as shown left |
| (9) sorbitan tristearate | 1.0 | same as shown left | same as shown left |
| (10) perfume | Proper amount | same as shown left | same as shown left |

Manufacturing Method

The components (1) to (5), excluding mica titanium (3), were mixed in a hencyl mixer and pulverized in a atomizer. To this mixture was added mica titanium (3) and, to the resulting mixture, a homogenized mixture of the components (6) to (10) was added and mixed homogeneously. The resulting mass was pulverized by an atomizer and sieved and the resulting mass was compression-molded onto a saucer to produce powdered eye-shadow.

The powdered eye-shadow of the Comparative Examples 10 and 11 were heavy and powdery, whereas the powdered eye-shadow of Example 10 presented extremely smooth tactile feeling and optimum affinity.

The composition of the lotion is shown in Table 6.

TABLE 6

| Composition | Ex. 11 | Comp. Ex. 12 |
| --- | --- | --- |
| (1) octamethyl cyclo tetrasiloxane | 25.0 | same as shown left |
| (2) dimethyl polysiloxane (6 cps) | 8.0 | same as shown left |
| (3) squalane | 4.5 | same as shown left |
| (4) polyglyceryl diisostearate | 1.5 | same as shown left |
| (5) dimetyl polysiloxane polyoxyalkylene polymer (HLB = 3) | 5.0 | same as shown left |
| (6) butyl paraben | 0.3 | same as shown left |
| (7) talc of Ex. 4 or Comp. Ex. 2 | 0.5 | same as shown left |
| (8) silica beads of Ex. 4 or Comp. Ex. 2 | 3.0 | same as shown left |
| (9) pure water | Balance for 100.0 | same as shown left |
| (10) propylene glycol | 9.0 | same as shown left |
| (11) glycerine | 4.5 | same as shown left |
| (12) methyl paraben | 0.2 | same as shown left |
| (13) perfume | Proper amount | same as shown left |

Manufacturing Method

To an oily phase obtained on mixing the components (1) to (6) at room temperature were added (7) and (8) and dispersed homogeneously. An aqueous phase obtained on homogeneously mixing and dissolving the components (9) to (12) was added gradually to the oily phase and homogeneously dispersed by a homogenizing mixer and emulsified particles were adjusted and added to with (13) to produce a lotion.

The lotion of the Comparative Example 12 was poor in spreadability and exhibits a tense feeling after application. Conversely, the lotion of Example 11 is excellent in spreadability and exhibits a moisturized feeling on application. The lotion of Example 11 exhibited optimum affinity to the skin.

The composition of the moisturizing cream is shown in Table 7.

TABLE 7

| Composition | Ex. 12 | Comp. Ex. 13 |
| --- | --- | --- |
| (1) octamethyl cyclo tetrasiloxane | 20.0 | same as shown left |
| (2) methyl phenyl polysiloxane | 5.0 | same as shown left |
| (3) squalane | 6.0 | same as shown left |
| (4) cetyl-2-ethyl hexanoate | 2.5 | same as shown left |
| (5) dimethyl polysiloxane polyoxyalkylene polymer (HLB = 3) | 4.5 | same as shown left |
| (6) butyl paraben | 0.3 | same as shown left |
| (7) sericite of Ex. 5 or Comp. Ex. 3 | 5.0 | same as shown left |
| (8) pure water | balance | same as shown left |
| (9) 1,3-butylene glycol | 7.0 | same as shown left |
| (10) glycerine | 5.0 | same as shown left |
| (11) PCA soda*1 | 2.0 | same as shown left |
| (12) sodium hyaluronate | 0.1 | same as shown left |
| (13) methyl paraben | 0.2 | same as shown left |
| (14) perfume | proper amount | same as shown left |

*1 is sodium pyrrolidone carboxylate.

Manufacturing Method

To an oily phase obtained on mixing the components (1) to (6) at room temperature was added the component (7) and dispersed homogeneously. An aqueous phase obtained on homogeneously mixing and dissolving the components (8) to (13) was added gradually to the oily phase and homogeneously dispersed by a homogenizing mixer and emulsified particles were adjusted and added to with (14) to produce a moisturizing cream.

The moisturizing cream of the Comparative Example 13 was poor in spreadability and exhibits a tensile application feeling. Conversely, the moisturizing cream of Example 12 is excellent in spreadability and exhibits a moisturized feeling on application and optimum affinity to the skin.

The composition of liquid foundation is shown in Table 8.

TABLE 8

| Composition | Ex. 13 | Comp. Ex. 14 |
| --- | --- | --- |
| (1) decamethyl cyclopentasiloxane | 22.0 | same as shown left |
| (2) octamethyl cyclotetrasiloxane | 18.0 | same as shown left |
| (3) methylphenyl polysiloxane | 7.0 | same as shown left |
| (4) dimethyl polysiloxane polyoxyalkylene polymer (HLB = 3) | 1.0 | same as shown left |
| (5) octyl methoxy cyanate | 3.0 | same as shown left |
| (6) colored pigment of Ex. 6 or Comp. Ex. 4 | proper amount | same as shown left |
| (7) titanium dioxide of Ex. 6 or Comp. Ex. 4 | 8.5 | same as shown left |
| (8) talc of Ex. 6 or Comp. Ex. 4 | 3.7 | same as shown left |
| (9) butyl paraben | 0.3 | same as shown left |
| (10) pure water | balance | same as shown left |
| (11) glycerine | 5.5 | same as shown left |
| (12) ethanol | 11.0 | same as shown left |

TABLE 8-continued

| Composition | Ex. 13 | Comp. Ex. 14 |
|---|---|---|
| (13) methyl paraben | 0.2 | same as shown left |
| (14) perfume | proper amount | same as shown left |

Manufacturing Method

The components (6) to (8) were previously mixed together and pulverized. The pulverized components (6) to (8) were added to an oily phase obtained on homogeneously dissolving the components (1) to (5) at room temperature and dispersed homogeneously. An aqueous phase obtained on homogeneously dissolving the components (9) to (13) was added gradually to the oily phase and homogeneously dispersed by a homogenizing mixer and emulsified particles were adjusted and added to with (14) to produce a liquid foundation.

The liquid foundation of the Comparative Example 14 was poor in spreadability and exhibits a tensioned application feeling. Conversely, the moisturizing cream of Example 13 was excellent in spreadability and exhibits a moisturized feeling on application and optimum affinity to the skin.

The composition of solid face powders is shown in Table 9:

TABLE 9

| Composition | Ex. 14 | Comp. Ex. 15 |
|---|---|---|
| (1) mica of Ex. 7 or Comp. Ex. 5 | 22.0 | same as shown left |
| (2) talc of Ex. 7 or Comp. Ex. 5 | to 100.0 | same as shown left |
| (3) titanium dioxide of Ex. 7 or Comp. Ex. 5 | 2.0 | same as shown left |
| (4) vaseline | 4.0 | same as shown left |
| (5) octyl dodecyl oleate | 3.5 | same as shown left |
| (6) sorbitan sesquioleate | 0.3 | same as shown left |
| (7) perfume | proper amount | same as shown left |

Manufacturing Method

The components (1) to (7) were mixed homogeneously to serve as a base for powdery cosmetics. 55 wt % of ethanol were added to the base for the powdery cosmetics and mixed homogeneously. The resulting mass was charged into a saucer and molded under suction. The resulting molded particle was dried for 24 hours at a temperature of 40° C. to solid face powders.

The solid face powders of the Comparative Example 15is heavy in spreadability and powdery on application. Conversely, the solid face powders of Example 14 were excellent in spreadability and in affinity to the skin on application.

The composition of a face-washing foam is shown in Table 10:

TABLE 10

| Composition | Ex. 15 | Comp. Ex. 16 |
|---|---|---|
| (1) sericite of Ex. 1 or Comp. Ex. 1 | 2.0 | same as shown left |
| (2) stearic acid | 1.0 | same as shown left |
| (3) amisoft MK-11*[1] | 20.0 | same as shown left |
| (4) 1,3-butylene glycol | 33.0 | same as shown left |
| (5) pure water | to 100.0 | same as shown left |
| (6) PEG20000 | 10.0 | same as shown left |

*[1] is potassium N-myristoyl-L-glutamate, manufactured by AJINOMOTO KK.

Manufacturing Method

The components (2) to (4) were mixed together and dissolved to give a solution into which the component (1) was dispersed. The component (6) was heated and dissolved in the component (5). The resulting mass was added to the components (1) to (4) to give a face-washing foam.

The face-washing foam of the Comparative Example 16 exhibited powdery feeling after use for face washing. Conversely, the face-washing foam of Example 15 exhibited a moisturized feeling after use for face washing and optimum affinity to the skin.

The composition of a body shampoo is shown in Table 11.

TABLE 11

| Composition | Ex. 16 | Comp. Ex. 17 |
|---|---|---|
| (1) sericite of Ex. 2 or Comp. Ex. 2 | 2.0 | Same as shown left |
| (2) amisoft CT-12*[1] | 12.0 | Same as shown left |
| (3) softazline CH*[2] | 40.0 | Same as shown left |
| (4) amizole LDE*[3] | 2.0 | same as shown left |
| (5) concentrated glycerine | 4.0 | same as shown left |
| (6) PCA soda | 1.0 | same as shown left |
| (7) pure water | to 100.0 | same as shown left |

*[1] is N-palm oil fatty acid-L-glutamic acid triethanol amine, manufactured by AJINOMOTO KK.
*[2] is 2-alkyl-N-carboxymethyl-N-hydroxy methyl imidazlium betain, manufactured by KAWAKEN FINE CHEMICAL KK.
*[3] cocoyl diethanoylamide, manufactured by KAWAKEN FINE CHEMICAL KK.

Manufacturing Method

The components (2) to (5) were mixed and dissolved to give a solution into which the component (1) was dispersed. The component (6) was mixed with the component (7), and was added to the dispersion of components (1) to (5) to give a body shampoo.

The body shampoo of Comparative Example 17 presented tensioned feeling after use for washing. Conversely, the face-washing foam of Example 16 presented moisturized feeling and optimum affinity to the skin after use.

The composition of kneaded perfume is shown in Table 12.

TABLE 12

| Composition | Ex. 17 | Comp. Ex. 18 |
|---|---|---|
| (1) silica beads of Ex. 3 or Comp. Ex. 3 | 1.5 | same as shown left |
| (2) titanium dioxide of Ex. 3 or Comp. Ex. 3 | 1.5 | same as shown left |
| (3) red No. 202 | 0.05 | same as shown left |
| (4) vaseline | 9.4 | same as shown left |
| (5) squalane | To 100.0 | same as shown left |
| (6) microcrystalline wax | 15.0 | same as shown left |
| (7) methylphenyl polysiloxane | 9.0 | same as shown left |
| (8) perfume | 15.0 | same as shown left |

Manufacturing Method

The components of (4) to (7) were dissolved on heating to 85° C. and mixed homogeneously. To the resulting mixture were added (2) and (3) and dispersed by three rolls. The resulting dispersion was transferred to a vacuum kiln into which (1) was added and dispersed homogeneously. To the resulting dispersion was added perfume and defoamed. The resulting mass was poured into a vessel and quenched to give a kneaded perfume.

The kneaded perfume of Comparative Example 18 was heavy in spreadability and powdery, while the kneaded perfume of Example 17 was satisfactory in spreadability and in affinity to the skin.

The composition of the hair treatment agent is shown in table 13.

TABLE 13

| Composition | Ex. 18 | Comp. Ex. 19 |
|---|---|---|
| (1) silica beads of Ex. 4 or Comp. Ex. 4 | 5.0 | same as shown left |
| (2) low boiling point isoparaffin | to 100.0 | same as shown left |
| (3) leopearl KL*[1] | 5.0 | same as shown left |
| (4) methyl phenyl polysiloxane | 2.5 | same as shown left |
| (5) ethanol | 6.5 | same as shown left |
| (6) collagen hydrolyzate | 0.01 | same as shown left |
| (7) silicone elastomer | 2.0 | same as shown left |

*[1] is dextrin palmitate manufactured by CHIBA SEIFUN KK.

Manufacturing Method

The components (1), (2), (3) and (9) were dissolved on heating to 80° C. and dispersed homogeneously. To the resulting dispersion was added and mixed (4). To the resulting mixture were added (5) and (6) and dispersed and mixed homogeneously. 85 parts of thus obtained raw liquid and 15 parts of LPG were charged into an aerosol vessel to give a hair treatment agent.

The smooth tactile feeling and affinity to the skin of the inventive coated pigments and extender pigments in dosage form were checked.

The hair treatment agent of Comparative Example 19 was powdery and showed poor affinity, while that of Example 18 could smooth the hair and presented affinity to the hair.

The following test was conducted to check the effect in the cosmetics of the inventive coated pigments and extender pigments as to smoothness of tactile feeling and affinity to the skin and hair. (Test on smoothness of two at way foundation, liquid foundation and moisturizing cream)

The pigments and extender pigments was applied on a 8 cm by 5 cm collagen paper sheet manufactured by IDEMITSU KAGAKU under the trade name of "SUPPLALE" at a amount of 1 $mg/cm^2$, and set on a reciprocating the friction coefficient measurement tester manufactured by KATO-TEC. A non-coated collagen sheet was set and placed under a load of 50 $g/cm^2$. The resulting assembly was reciprocated five times to find a mean value of the five coefficient values (MIU). This operation was repeated thrice to find the mean value. (Test on Smoothness of the hair treatment agent)

15 hairs were bonded at 1 mm interval at distance to each other on a slide glass. The hair treatment agent was sprayed for five seconds on the hairs to produce sprayed samples which were then set on a reciprocating friction coefficient measurement tester manufactured by KATO-TEC. A non-coated collagen sheet was set and placed under a load of 30 $g/cm^2$. The resulting assembly was reciprocated five times to find a mean value of the five coefficient values (MIU). In consideration of measurement variations, the above operation was repeated thrice to find the mean value. (Test on affinity to skin or hair)

The spreadability on application, slippery feeling and moisture feeling on application as well as application feeling as evaluation items were evaluated by 30 panellers in accordance with the following standards:
(Evaluation points)
excellent 4 points
good 3 points
acceptable 2 points
poor 1 point
very poor 0 point
(Judgment)
average point of 3.0 to 4.0 ⊚
average point of 2.0 to 3.0 ◯
average point of 1.0 to 2.0 Δ
average point of 0 to 1.0 X
The results are shown in tables 14 to 21.

TABLE 14

Results of two way foundation

| Samples | MIU | Spreadability | Smoothness | Moist Feeling | Application Feeling |
|---|---|---|---|---|---|
| Ex. 9 | 1.76 | ⊚ | ⊚ | ⊚ | ⊚ |
| Comp. Ex. 8 | 2.43 | x | x | ○ | Δ |
| Comp. Ex. 9 | 2.34 | x | x | Δ | Δ |

TABLE 15

Results of powdered eye shadow

| Samples | MIU | Spreadability | Smoothness | Moist Feeling | Application Feeling |
|---|---|---|---|---|---|
| Ex. 10 | 1.53 | ⊚ | ⊚ | ⊚ | ⊚ |
| Comp. Ex. 10 | 2.24 | x | x | Δ | Δ |
| Comp. Ex. 11 | 2.38 | x | x | Δ | Δ |

TABLE 16

Results of Lotion

| Samples | MIU | Spread-ability | Smooth-ness | Moist Feeling | Application Feeling |
|---|---|---|---|---|---|
| Ex. 11 | 1.36 | ⊚ | ⊚ | ⊚ | ⊚ |
| Comp. Ex. 12 | 1.76 | Δ | Δ | x | Δ |

TABLE 17

Results of moisturizing cream

| Samples | MIU | Spread-ability | Smooth-ness | Moist Feeling | Application Feeling |
|---|---|---|---|---|---|
| Ex. 12 | 1.21 | ⊚ | ⊚ | ⊚ | ⊚ |
| Comp Ex. 13 | 1.87 | x | x | ○ | Δ |

TABLE 18

Results of liquid foundation

| Samples | MIU | Spread-ability | Smooth-ness | Moist Feeling | Application Feeling |
|---|---|---|---|---|---|
| Ex. 13 | 1.13 | ⊚ | ⊚ | ⊚ | ⊚ |
| Comp. Ex. 14 | 2.05 | x | x | Δ | Δ |

TABLE 19

Results of sold face powders

| Samples | MIU | Spread-ability | Smooth-ness | Moist Feeling | Application Feeling |
|---|---|---|---|---|---|
| Ex. 14 | 1.87 | ⊚ | ⊚ | ⊚ | ⊚ |
| Comp. Ex. 15 | 2.30 | x | x | Δ | Δ |

TABLE 20

Results of kneaded perfume

| Samples | MIU | Spread-ability | Smooth-ness | Moist Feeling | Application Feeling |
|---|---|---|---|---|---|
| Ex. 17 | 2.35 | ○ | ○ | ⊚ | ⊚ |
| Comp. Ex. 18 | 2.57 | x | Δ | x | x |

TABLE 21

Results of hair treatment agent

| Samples | MIU | Spread-ability | Smooth-ness | Moist Feeling | Application Feeling |
|---|---|---|---|---|---|
| Ex. 18 | 1.26 | ○ | ○ | ⊚ | ⊚ |
| Comp. Ex. 19 | 1.60 | x | x | x | x |

Effect of the Invention

As described above, the coated pigments and extender pigments of the present invention is the coated pigments and extender pigments processed with a mixture at least containing N-acyl forms of at least 14 amino acids present in nature. Of these amino acids, only glycine has no isomeric form of the L-form, other amino acids being the L-forms. The N-acyl forms may also be in the form of salts. The pigments and extender pigments obtained in the present invention exhibits smooth tactile feeling and extremely smooth tactile feeling when used in the cosmetics, thus presenting satisfactory application feeling to the skin or hair and excellent affinity to the skin or hair. By application of the pigments and extender pigments (pulverized material) in the present invention, it is possible to provide cosmetics having these superior properties.

What is claimed is:

1. Coated pigments and extender pigments usable in cosmetics comprising pigments and extender pigments, said pigments and extender pigments being coated with a mixture comprising at least N-acyl forms of 14 amino acids specified by glycine, L-alanine, L-valine, L-leucine, L-isoleucine, L-phenylalanine, L-proline, L-threonine, L-serine, L-arginine, L-histidine, L-lysine, L-aspartic acid and L-glutamic acid, wherein said N-acyl form may be in the salt form.

2. The coated pigments and extender pigments as defined in claim 1 wherein at least a part of said 14 amino acids is at least one of amino acids which can be obtained from a total hydrolysate of protein.

3. The coated pigments and extender pigments as defined in claim 2 wherein said protein is at least one of animal proteins, and plant proteins, containing said 14 amino acids as main amino acid constituents.

4. The coated pigments and extender pigments as defined in claim 1 wherein said mixture comprising at least N-acyl forms of said 14 amino acids comprises at least 14 acylated amino acids represented by the following general formula:

$$R_2CHCOOM \atop | \atop HNCOR_1 \qquad (1)$$

being obtainable by acylating amino acids containing at least the 14 amino acids which can be obtained on total hydrolysis of at least one protein type, where in the general formula $R_1$ is an alkyl group or a hydrocarbon group having the alicyclic structure, in the carbons of C8 to C22, saturated or unsaturated, $$R_2CHCOO \atop | \atop HN$$

is an amino acid residue, specifically, any of glycine, alanine, valine, leucine, isoleucine, phenylalanine, proline, threonine, serine, arginine, histidine, lysine, aspartic acid and glutamic acid residues, and M is any one of H, metal, ammonium and an onium of organic alkanol amine.

5. The coated pigments and extender pigments as defined in claim 1 wherein at least a part of said 14 amino acids is one or more amino acids obtainable or obtained on total hydrolysis of protein derived from at least one of silk and pearl.

6. The coated pigments and extender pigments as defined in claim 1 wherein said pigments and extender pigments is coated with a mixture comprising N-acyl forms of amino acids obtained on total hydrolysis of at least one of proteins enumerated by silk, pearl, collagen, keratin, wheat and soybean.

7. Cosmetics comprising the coated pigments and extender pigments as defined in any one of claims 1 to 6.

8. The coated pigments and extender pigments according to claim 3 wherein said animal proteins are selected from the group consisting of silk and pearl.

9. The coated pigments and extender pigments according to claim 3 wherein said plant proteins are selected from the group consisting of wheat and soybean.

* * * * *